United States Patent [19]

Helbig et al.

[11] Patent Number: 4,546,195

[45] Date of Patent: Oct. 8, 1985

[54] PROCESS FOR THE PRODUCTION OF AMINO-DICARBOXYLIC ACID-BIVALENT METAL-HALOGEN COMPLEXES AND SUCH COMPLEXES

[75] Inventors: Joachim Helbig, Tutzing; Hubert Schmidbaur, Garching, both of Fed. Rep. of Germany

[73] Assignee: Verla-Pharm, Arzneimittelfabrik, Apotheker H.J.v. Ehrlich GmbH & Co. KG, Tutzing, Fed. Rep. of Germany

[21] Appl. No.: 540,644

[22] Filed: Oct. 11, 1983

[30] Foreign Application Priority Data

Oct. 14, 1982 [DE] Fed. Rep. of Germany ....... 3238118

[51] Int. Cl.[4] .......................... C07F 3/06; C07F 11/06
[52] U.S. Cl. ....................................... 556/50; 556/133
[58] Field of Search ..................... 260/429 R, 429.9; 562/553

[56] References Cited

U.S. PATENT DOCUMENTS 2,849,468 8/1958 Cardinal ........................... 260/429.9
2,996,490 8/1961 Rowland et al. ............ 260/429 R X
3,285,953 11/1966 Wasserman et al. ............. 260/429.9

OTHER PUBLICATIONS

Chemical Abstracts, 80, 96355v; 146542b; 60172u; 41815q (1974).
Chemical Abstracts, 83, 37574e; 193729q (1975).
Chemical Abstracts, 85, 182413x (1976).
Chemical Abstracts, 78, 8561q (1973).
Chemical Abstracts, 94, 77625f (1981).
Chemical Abstracts, 89, 127010w (1978).
Chemical Abstracts, 87, 29887b (1977).
Chemial Abstracts, 88, 41680g (1978).

*Primary Examiner*—Helen M. S. Sneed
*Attorney, Agent, or Firm*—Burns, Doane, Swecker & Mathis

[57] ABSTRACT

The invention concerns a novel process for the production of a complex compound comprising an amino-dicarboxylic acid ion component, a bivalent metal ion component, and a halogen ion component, which comprises the step of reacting together in an aqueous medium an amino-dicarboxylic acid compound, a bivalent metal compound, and a halogen compound, the proportions of said compounds being chosen so that one of each of said ion components is comprised in the aqueous medium, the bivalent metal compound being selected from the oxide, hydroxide, carbonate or a halide of the bivalent metal, and the halogen compound being said halide of the bivalent metal or a hydrogen halide. Certain of the complexes are novel and find use in a variety of medical and veterinary fields.

7 Claims, No Drawings

PROCESS FOR THE PRODUCTION OF AMINO-DICARBOXYLIC ACID-BIVALENT METAL-HALOGEN COMPLEXES AND SUCH COMPLEXES

This invention relates to a process for the production of amino-dicarboxylic acid-bivalent metal-halogen complexes and novel such complexes, which novel complexes may be obtained by the process of the invention or by processes analogous to known processes.

BACKGROUND OF THE INVENTION

A process for the production of certain magnesium amino-dicarboxylic acid-halogen complexes of the nature of the present invention is disclosed in U.S. Pat. No. 4,137,326. This process involves reaction in an aqueous medium of a magnesium salt of the corresponding amino-dicarboxylic acid with a magnesium halide. For the purpose of obtaining a solid form of the resulting magnesium-amino-dicarboxylic acid halogen complex, a spray-drying procedure may be followed. This process requires the particular magnesium salt of the amino-dicarboxylic acid as starting material, which is relatively costly and which leads to the production cost of the desired final magnesium complex being relatively high.

It is an object of the present invention to provide a process for producing amino-dicarboxylic acid-bivalent metal-halogen complexes, such as and including the magnesium-amino-dicarboxylic acid-halogen complexes mentioned above, from less costly starting materials, leading to a less costly procedure for obtaining the desired complexes.

SHORT DESCRIPTION OF THE INVENTION

The present invention is based on the surprising finding that, in spite of the fact that it has been considered necessary to ensure that side-reactions are avoided to obtain such complexes, it is possible to obtain such complexes from starting materials which are considerably less costly than the bivalent metal amino-dicarboxylic acid. More particularly, it has been found that the desired complexes can be obtained when proceeding from starting materials of the bivalent metal selected from the oxide, hydroxide, carbonate, or halide thereof. Such bivalent metal compounds, it has been found in accordance with the invention, can be reacted in an aqueous medium with the particular amino-dicarboxylic acid and the desired metal or hydrogen halide to directly obtain the desired amino-dicarboxylic acid-bivalent metal-halogen complex. Essentially, all that is required in terms of the present invention is that equimolecular proportions of the amino-dicarboxylic acid, the bivalent metal and the halide be comprised in the aqueous medium. For example two mol equivalents of the amino-dicarboxylic acid comprised in an aqueous medium may be reacted with one mol equivalent of the bivalent metal oxide, hydroxide or carbonate of the bivalent metal and one mol equivalent of the bivalent metal halide. Another source of the halogen component in the final complex may be the respective hydrogen halide, in which case two alternatives are available; viz. reaction of two mol equivalents of the amino-dicarboxylic acid with two mol equivalents of the oxide, hydroxide or carbonate of the bivalent metal and with two mol equivalents of the hydrogen halide, or reaction of two mol equivalents of the amino-dicarboxylic acid with one mol equivalent of the oxide, hydroxide or carbonate of the bivalent metal and with a mixture of a further one mol equivalent of the oxide, hydroxide or carbonate of the bivalent metal and two mol equivalents of the hydrogen halide.

DETAILED DESCRIPTION OF THE INVENTION

The complex compounds which may be produced in accordance with the process of the present invention comprise an amino-dicarboxylic acid ion component, a bivalent metal ion component and a halogen ion component, in which the final complex compound structure includes one of each said ion components. The process, in accordance with the invention for obtaining such a complex compound comprises the step of reacting together in an aqueous medium an amino-dicarboxylic acid compound, a bivalent metal compound, and a halogen compound, the proportions of said compounds being chosen so that one of each of said ion components is present in the aqueous medium, the bivalent metal compound being selected from the oxide, hydroxide, carbonate or a halide of the bivalent metal, and the halogen compound being said halide of the bivalent metal or a hydrogen halide.

Although other less acidic amino-dicarboxylic acids may find application in the process of the invention under certain conditions and in combination with specific bivalent metal compounds and halides, specifically contemplated by the present invention are aspartic acid and glutamic acid and more particularly the L-forms thereof.

Similarly, although other bivalent metal compounds may find application in the process of the invention under certain conditions and in combination with specific amino-dicarboxylic acids and halides, specifically contemplated bivalent metal compounds contemplated by the present invention are the oxides, hydroxides, carbonates or halide of iron, strontium, cobalt, calcium, magnesium, barium, manganese and zinc. In this regard, it has for example been found that certain specific reactions contemplated by the process of the present invention do not proceed or do not proceed satisfactorily or with a satisfactory yield when the bivalent metal compound employed is a copper or tin compound. Furthermore, in view of somewhat limited applications in the medical and veterinary fields, bivalent metal compounds such as compounds comprising cadmium and mercury have not been examined in detail. Such bivalent metal complexes are however contemplated by the present invention since cadmium and mercury compounds may be employed as topical antiseptics, and cadmium compounds may furthermore be employed at low concentrations over a limited period as anthelmintics, for example at a concentration of less than 0.1% in feed for swine and poultry.

The complex compounds which may be obtained by the process of the present invention would in general be possessed of the following structure:

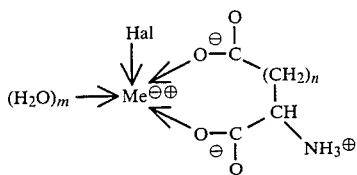

in which
Me is the bivalent metal,
m=0, 1, 2 or 3
n=1 or 2, and
Hal is a halogen.

Additional stability is gained from electrostatic interaction between the ammonium center and the halide ion (not shown in the formula).

The hydrate content of the complex compounds is specific to the substrate and m is for example 3 when Me is magnesium, Hal is chlorine and n is 1. When Hal is bromine, for example, m is 2. When Me is calcium and Hal is chlorine, m is 1 and when Me in zinc and Hal is chlorine, m is 0.

Of the above complex compounds, certain magnesium complexes are known, in particular from U.S. Pat. No. 4,137,326. Magnesium aspartate hydrochloride (manufactured by the process earlier described) is presently made available for use in human medicine and is more specifically employed to increase magnesium levels in man. Prophylaxis of cardiac infarct or cardiac reinfarct has been determined to be an exceptionally valuable indication for this compound. The analogous glutamate does not apparently possess this specific utility, but may also be employed at similar doses in magnesium therapy, which is gaining recognition. These compounds and more specifically the hydrochlorides additionally possess a sedative action which has found application in the veterinary field, for example as a feed additive for calming animals, in particular swine, before slaughter. Hypomagnesaemia in cattle may also be treated with the magnesium compounds of the invention. The dosage required depends on the host and the nature of the treatment, but in the case of the magnesium complex compounds will lie between about 5 and 20 mg/kg animal body weight. Suitable dosage forms for human medicine include infusion and intramuscular solutions, tablets, capsules and dragees, and granulates or liquid additive solutions are suitable for feed additives.

The barium complex compounds of the present invention possess cardiac muscle stimulating activity and may be employed at doses similar to those of the magnesium complex compounds. Barium compounds further find use, for example at an oral dose of about 1 to 2 mg/kg animal body weight as a cathartic or purgative in horses and may similarly be employed in treating cattle for bloat. The magnesium complex compounds also find application in this field.

The manganese compounds of the invention may be employed as hematinics, i.e. for increasing the number of red corpuscles in the blood, as may be required in the treatment of anaemia. The oral daily dose for this use is between about 0.5 and 5 mg/kg body weight for the complex compounds of the invention. The manganese compounds are furthermore useful in the prevention of perosis in poultry and up 100 mg/kg of poultry feed may be employed for this purpose.

The zinc complexes of the present invention would in general be employed topically as astringents or antiseptics. Ointments or solutions would comprise between about 1 and 5% by weight of the zinc complex. An intestinal antiseptic solution would comprise a similar concentration of the zinc complex.

The iron complex compounds of the invention find particular use as hematinics in the treatment of iron deficiency anaemia. The preferred dosage form is an intra-muscular solution and the dose, dependent on the condition of the subject, would be between about 1 and 4 mg/kg body weight.

The strontium complexes of the invention may be employed in a fashion similar to the above-mentioned zinc complexes as an astringent or antiseptic. Strontium complexes also find application in skeletal remineralisation or for replacement of radioactive strontium. A bromide form of the strontium complex, at an oral dose of between 1 and 2 g, possesses sedative activity, and diuretic activity is also observed at these doses.

The calcium complex compounds of the present invention are particularly suitable substances for calcium supplementation both in medical and veterinary fields. Doses required are well known, but based on the fact that resorption of the complexes of the invention in general appears to exceed that of other bivalent metal compounds, doses required can be lower. Bromide forms additionally possess a certain sedative action. Daily oral doses are between about 0.01 to 0.1 mg/kg animal body weight.

The following are illustrative Examples of process procedures which may be followed in producing the complex compounds of the present invention in accordance with the process of the invention:

EXAMPLE 1

Prodution of Magnesium aspartate hydrochloride 541 g of L-aspartic acid is dispersed in 1016 ml of deionised water in a beaker with stirring and heating to 60° C. 82 g of Magnesium oxide powder is added to this dispersion with further stirring. The temperature rises and the dispersion slowly becomes clear. After about 2 hours a practically clear solution is obtained, which is thereafter mixed with a solution of 413 g of magnesium chloride (MgCl$_2$.6H$_2$O) in 140 ml of water, whereafter the concentration of the disolved substances in the solution is adjusted by the addition of water to 30% by weight. The solution is filtered and then subjected to a spray-drying procedure with a laboratory spray-dryer (Buechi, Flawil) at an inlet temperature of 180° C. and a temperature of 120° C. in front of the cyclone.

Magnesium aspertate hydrochloride is obtained as a white powder, with 100% yield. The properties of this substance correspond exactly with the properties disclosed in Example 1 of U.S. Pat. No. 4,137,326, i.e. the two substances are identical.

EXAMPLE 2

Production of Magnesium glutamate hydrobromide 936 ml of deionised water is warmed to 60° C. in a beaker, and 484 g L-Glutamic acid is then added with stirring with a stirrer. 67 g of magnesium oxide powder is added to the resulting dispersion with continuous stirring. The temperature rises and the solution becomes clear after about 1 hour. To this solution is added a solution of 480 g of magnesium bromide-hexahydrate and 384 ml of water (35% by weight solution). The concentration of the complex in the solution is adjusted with water to 30% by weight. The solution is filtered through a G-3 sintered glass filter and then subjected to the spray-drying procedure described in Example 1.

Magnesium glutamate hydrobromide is obtained as a white powder, with 100% yield.

The following characteristics were determined:
Empirical formula: $C_5H_8BrNO_4Mg$.
Elemental analysis: $C_5H_8BrNO_4Mg.2H_2O$ (molecular weight 286,36): calculated: Mg 8.49, Br 27,90. found: Mg 8,68, Br 28,63.

the pH-value of a 13% by weight aqueous solution of the substance is 6,48.

EXAMPLE 3

Production of calcium aspartate hydrochloride 1010 ml of deionised water is warmed to 60° C., and 509 g L-aspartic acid is thereafter added with stirring. 142 g of calciumhydroxide in the form of a powder is added portion-wise with continuous stirring. The temperature rises further and the solution becomes clear after about 1 hour. 281 g calcium chloride-dihydrate in 325 ml of water (35% by weight solution) is added to this solution. The concentration, based on the complex, is adjusted to 30% by weight with water. The solution is then filtered through a G-3 sintered glass filter and spray-dried as described in Example 1.

Calcium aspartate hydrochloride is obtained in the form of a white powder with 100% yield.

Elemental analysis: $C_4H_6ClNO_4Ca.1H_2O$ (molecular weight 225,64): Calculated: Ca 17,76, Cl 15,71. found: Ca 18,35, Cl 15,90.

The pH-value of 13% by weight aqueous solution of the substance is 6,64.

EXAMPLE 4

Production of zinc aspartate hydrochloride 1025 g of deionised water is warmed to 60° C. and 464 g L-aspartic acid is added with stirring with a magnet stirrer. 142 g of zinc oxide in the form of a powder is added portion-wise with continuous stirring. The temperature rises slightly, but the solution does not become clear. The temperature was therefore increased to about 90° C., after which a clear solution was obtained. The concentration was decreased to 30% by weight by the addition of water.

The solution obtained is added to a solution of 238 g zinc chloride in 441 ml of water (35% by weight solution). The solution is adjusted with water to a concentration of 30% by weight, based on the complex. The solution is then filtered through a G-3 sintered glass filter and spray-dried as described in Example 1. Zinc aspartate hydrochloride is obtained in the form of a white powder, with 100% yield.

Elemental analysis: $C_4H_6ClNO_4Zn$ (molecular weight 232,92): calculated: Zn 28,07, Cl 15,22. found: Zn 28,39, Cl 14,77.

The pH-value of a 13% by weight aqueous solution of the substance is 4,2.

EXAMPLE 5

Production of magnesium aspartate hydrochloride 541 g L-aspartic acid is dispersed with stirring in 1016 ml of deionised water in a beaker, with heating to 60° C. 592 g of a 25% by weight hydrochloric acid solution and then 164 g of magnesium oxide powder is added to the dispersion and stirred. After a clear solution is obtained, this is filtered as described in Example 1 and spray-dried to recover the substance in the form of a white powder with 100% yield. The substance obtained is identical to that obtained by Example 1.

EXAMPLE 6

Production of strontium aspartate hydrochloride 431 g of L-aspartic is reacted in a fashion analogous to that described above with 239 g of strontium carbonate.

The reaction does not proceed very well, but the addition is filtered and the strontium content in the resulting solution is determined. (solution 1).

A strontium chloride solution (about 30% by weight) was prepared from 432 g of $SrCl_2.6H_2O$ and 424 g of water and the strontium content of this solution determined after filtration. (solution 2).

The two solutions, i.e. solution 1 and solution 2 are measured off so as each to comprise an equal amount of strontium and are then mixed together. The concentration of the solution subjected to spray-drying as described was about 25% by weight.

554 g of solid strontium compound comprising 31.5% of strontium was obtained. (Calculated for the monohydrate 32,1% Sr).

EXAMPLE 7

Production of calcium aspartate hydrobromide 435 g of aspartic acid is reacted in the fashion described above with 121 g of calcium hydroxide. The reaction proceeds relatively well. The pH of the resulting solution was adjusted from 5.3 to 5.9 and after filtration the calcium content determined. (solution 1).

A calcium bromide solution was prepared from 386 g of $CaBr_2.2H_2O$ and 549 g of deionised water, and the calcium content determined after filtration. (solution 2).

After adjusting the solutions 1 and 2 to comprise equal amounts of calcium, these were mixed together and the resulting solution adjusted to a 30% by weight concentration.

Spray drying does not proceed very well with a 30% solution, but proceeds with a less concentrated solution and different spray-drying conditions.

EXAMPLE 8

Production of barium aspartate hydrochloride 371 g of aspartic acid was reacted with 440 g of barium hydroxide ($Ba(OH)_2.8H_2O$) comprising 191.7 g of barium. The reaction between the two substances proceeds relatively well. (solution 1).

A barium chloride solution was prepared from 341 g of barium chloride ($BaCl_2.2H_2O$) and 628 g of water. The barium content was determined after filtration. (solution 2).

After adjusting the solutions 1 and 2 to comprise equal amounts of barium, the two solutions were mixed together. The end-concentration was about 19% by weight. After a few minutes a substance began to crystalize out. The solution was therefore warmed and immediately filtered.

EXAMPLE 9

Production of manganese aspartate hydrochloride 482 g of apartic acid was reacted with 220 g of manganese carbonate (99.7 g Mn). The reaction proceeds very poorly. (solution 1).

358 g of MnCl$_2$.4H$_2$O (99.4 g Mn) was dissolved in 292 g of water. The manganese content was determined after filtration. (solution 2).

After adjustment of the solutions 1 and 2 to comprise the same Mn content, these were mixed together. The end concentration was about 26% by weight.

Spray-drying led to a very voluminous product. 784 g of spray-dried substance comprising 22.9% mn was obtained (calculated for the monohydrate 22,85% Mn).

What we claim is:

1. A complex compound of the formula (H$_2$O)$_m$Me[OOC(CH$_2$)CH(NH$_2$)COO]H.Hal wherein Me is calcium, zinc or manganese; Hal is chlorine or bromine, and m=0-3.

2. A process for preparing complex compounds having a 1:1:1 ratio of amino-dicarboxylic acid ions, bivalent metal ions and halogen ions comprising the steps of:
(I) directly combining in an aqueous solution
 (i) an amino-dicarboxylic acid selected from the group consisting of glutamic acid and aspartic acid;
 (ii) at least one of oxides, hydroxides and carbonates of a metal selected from the group consisting of magnesium, calcium, strontium, zinc and manganese; and
 (iii) at least one of
  (A) chlorides, bromides or iodides of said metal; and
  (B) hydrochloric acid, hydrobromic acid or hydroiodic acid; and
(II) spray drying said aqueous solution.

3. A process according to claim 2, in which one mol equivalent of the amino-dicarboxylic acid compound is first reacted with one mol equivalent of the oxide, hydroxide or carbonate of the bivalent metal, and then with one mol equivalent of a halide of hydrogen.

4. A process according to claim 2, in which two mol equivalents of the amino-dicarboxylic acid is first reacted with one mol equivalent of the oxide, hydroxide or carbonate of the bivalent metal, and then with one mol equivalent of a halide of the bivalent metal.

5. A process according to claim 2, in which two mol equivalents of the amino-dicarboxylic acid is first reacted with one mol equivalent of the oxide, hydroxide or carbonate of the divalent metal, and then with a mixture made up of one mol equivalent of the oxide, hydroxide or carbonate of the bivalent metal and two mol equivalents of a halide of hydrogen.

6. A process according to claim 2, in which the reaction is carried out at a temperature of from 20° to 90° C.

7. A process according to claim 2, in which the aqueous medium resulting from the reaction is sterilized and rendered isotonic for use as an injectable solution.

* * * * *